United States Patent [19]
Freeman

[11] Patent Number: 5,201,776
[45] Date of Patent: Apr. 13, 1993

[54] ORTHOPAEDIC AND PROSTHETIC JOINT
[75] Inventor: Mark Freeman, Camberley, England
[73] Assignee: Hugh Steeper Limited, England
[21] Appl. No.: 776,617
[22] Filed: Oct. 15, 1991
[30] Foreign Application Priority Data
Oct. 23, 1990 [GB] United Kingdom ............... 9023038
[51] Int. Cl.⁵ .............................................. A61F 2/64
[52] U.S. Cl. .................................... 623/46; 623/39; 602/26
[58] Field of Search ...................... 623/39, 43–46; 602/26

[56] References Cited
U.S. PATENT DOCUMENTS

| | | | |
|---|---|---|---|
| 1,847,823 | 3/1932 | Dresser | 623/43 X |
| 3,806,958 | 4/1974 | Gusev | 623/46 X |
| 3,820,169 | 6/1974 | Long et al. | 623/39 |
| 4,144,881 | 3/1979 | Chappell | 602/26 X |
| 4,215,442 | 8/1980 | Blatchford et al. | 623/39 |
| 4,310,932 | 1/1982 | Näder et al. | 623/39 |
| 4,911,709 | 3/1990 | Marlow et al. | 623/39 |
| 4,961,416 | 10/1990 | Moore et al. | 602/26 |

FOREIGN PATENT DOCUMENTS

| | | | |
|---|---|---|---|
| 1008554 | 5/1952 | France | 623/39 |
| 0461635 | 8/1951 | Italy | 623/39 |
| 1109153 | 8/1984 | U.S.S.R. | 623/44 |
| 2151481 | 7/1985 | United Kingdom | 623/43 |

*Primary Examiner*—David Isabella
*Assistant Examiner*—D. Willse
*Attorney, Agent, or Firm*—Kinzer, Plyer, Dorn, McEachran & Jambor

[57] ABSTRACT

An orthopaedic or prosthetic joint comprising a linkage having a number of fixed-length links and a spring link of variable length, wherein there are five fixed-length links which are pivotally connected together in a geometric pattern such that the spring link acts to hold the joint in any one of a number of angles of flexion.

6 Claims, 2 Drawing Sheets

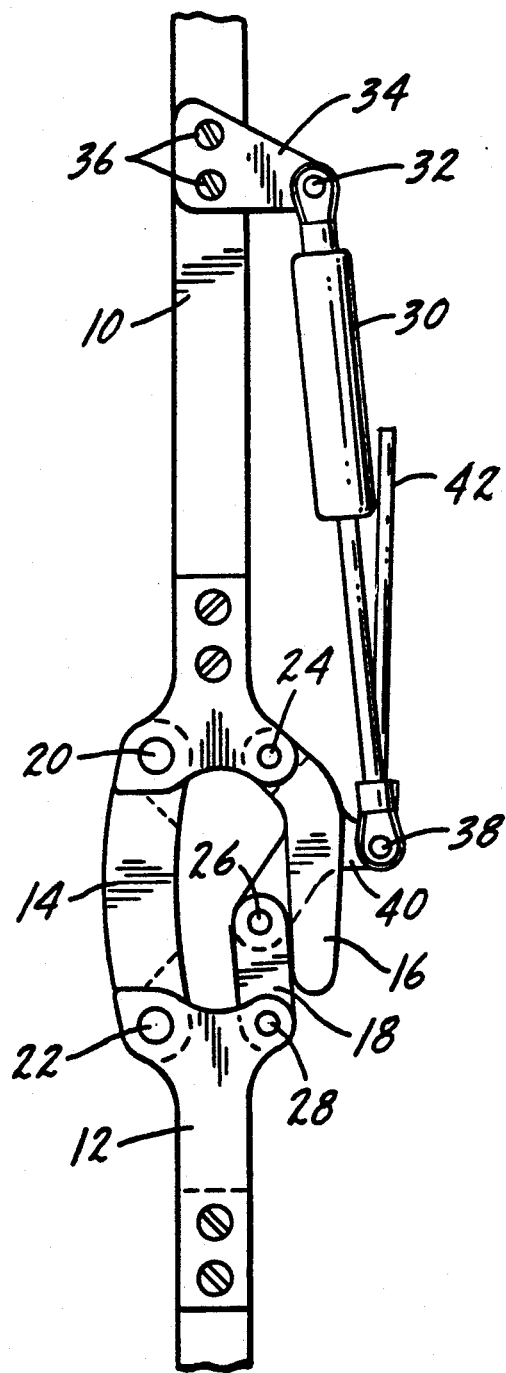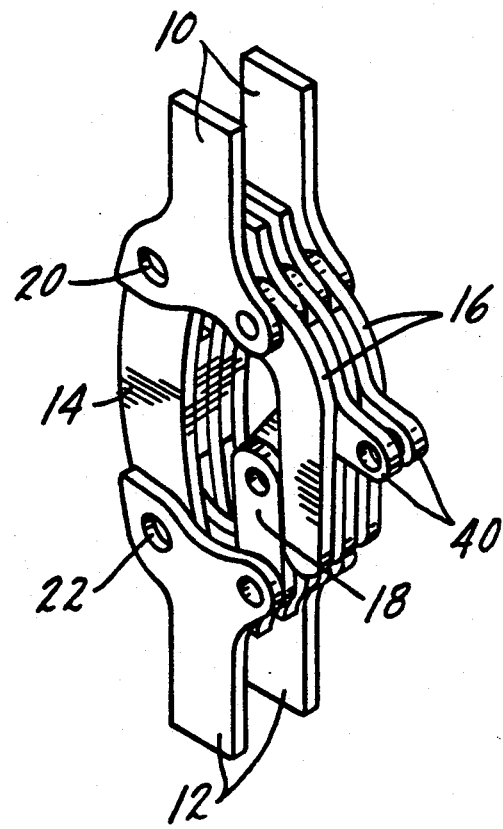

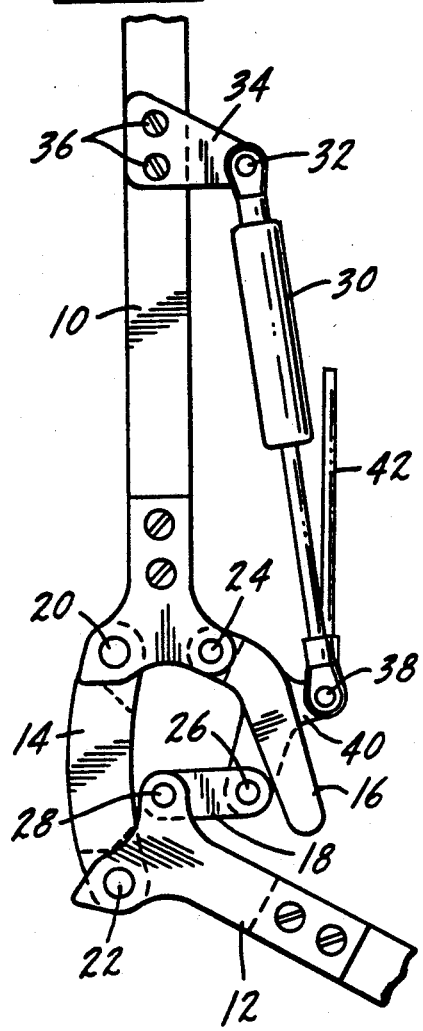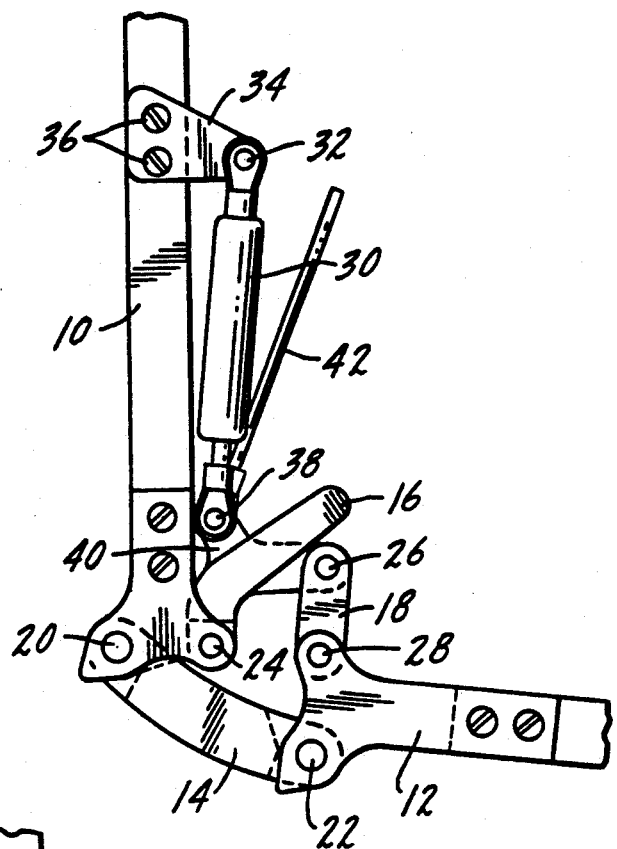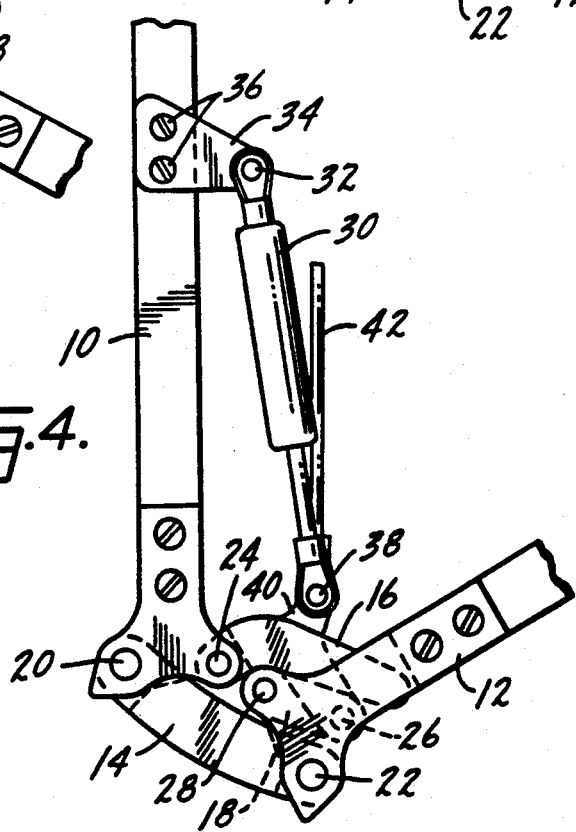

ORTHOPAEDIC AND PROSTHETIC JOINT

This invention relates to an orthopaedic or prosthetic joint, especially a knee joint.

In GB-A-2 206 494 we have described an orthosis or prosthesis for co-ordinating limb movement which comprises a hip joint and a knee joint. The orthosis or prosthesis thereby provides means for assisting a patient in moving between sitting and standing positions, and it also provides a natural and efficient method of ambulation for paraplegic patients. In the particular "walking braces" illustrated in GB-A-2 206 494, the movement of the hip and knee joints is co-ordinated by means of a cable or rod with knee extension being ensured by a spring member co-operating with automatically-engaging knee locks to prevent flexion of the knee. There are also hand-operated locks for the hips.

It is therefore a characteristic of the knee joint described in the said Patent Application that specific lock positions are required for each flexion position of the knee, with the result that inadvertent operation of the knee locks can result in a forceful extension of the knee.

The aim of the present invention is to provide an improved orthopaedic or prosthetic joint—especially a knee joint—which is not subject to a forceful unwanted extension of the knee.

With this aim in view, the invention is directed to an orthopaedic or prosthetic joint which comprises five fixed-length links and one spring link, the geometry of which is such that the spring acts to hold the joint in any one of a number of angles of flexion.

Preferably the geometry of the linkage is such that the spring is able to lock the joint in any selected position so that it cannot be flexed without an independent operation to release the joint.

An example of a specific knee joint in accordance with the invention is shown in the accompanying drawings, FIG. 1 is a side view of the knee joint in the "standing-up" position;

FIG. 2 is a similar view of the knee joint with the shin member at an angle of about 45° to the horizontal;

FIG. 3 is a similar view to the knee joint with the shin member at a position where it is substantially horizontal;

FIG. 4 is another side view of the knee joint with the shin member at an angle where it has swung about 30° upwards beyond the horizontal position; and FIG. 5 is an enlarged perspective view of a modification of the invention.

The knee joint shown in the drawings comprises a thigh member 10 and a shin member 12 which are interconnected by three fixed-length links 14, 16 and 18. Thus, the linkage 14 is pivotally connected at 20 to the thigh member 10 and is pivotally connected at 22 to the shin member 12. The link 16 is pivotally connected at 24 to the thigh member 10 and is pivotally connected at 26 to the remaining link 18 which, in turn, is pivotally connected at 28 to the shin member 12. It will therefore be seen that the joint comprises five fixed-length links, namely, the links 10, 12, 14, 16 and 18.

The joint is completed by a spring link 30 which is pivotally connected at 32 to a projection or lug 34 which is fastened by screws 36 to a part of the thigh member 10 remote from the pivot joints 20 and 24. The lower end of the spring link 30 is pivotally connected at 38 to a nose portion 40 on the link 16. The spring link 30 is of telescopic construction in this particular embodiment and preferably take the form of a gas spring. It could however equally include a helical spring member as in GB-A-2 206 494.

The geometry of the five fixed-length links and the spring link is such that the spring link is able to hold the joint in any one of a number of angles of flexion. Furthermore, the geometry is also such that the spring link 30 is able to lock the knee joint in the fully extended position (FIG. 1) so that it cannot be flexed without an independent operation to release the joint. Such independent operation is effected by means of a cable or rod 42 attached to the nose portion 40 of the link 16 at the pivotal connection 38.

FIGS. 2–4 show three specific positions into which the knee joint shown in FIG. 1 can be moved on operation of the cable or rod 42. Thus, FIG. 2 shows the shin member 12 at a position of about 45° to the horizontal, FIG. 3 shows the shin member substantially horizontal, and FIG. 4 shows the shin member at an angle where it has swung about 30° beyond the horizontal position. In each case, the five fixed-length links 10, 12, 14, 16 and 18 co-act under the influence of the spring pressure from the spring link 30 to hold themselves in the respective position shown. The cable or rod 42 is operated by the hips of the patient or by other means so that, when the cable or rod is pulled, it causes the line of action of the patient's weight to move from in front of the pivoted connections 24, 26, 28 to behind them, thereby allowing flexion to occur.

Although the invention has been described above in relation to a knee joint, it is to be understood that it is applicable to orthopaedic and prosthetic joints generally. The specific knee joint shown in the drawings has been especially designed for use by children, but it is to be understood that a knee joint for use by adults will be similar in construction and operation.

Where the joint of the invention is applied to a complete reciprocating gait orthosis or prosthesis as described in GB-A-2 206 494, it is to be understood that such a knee joint will be provided for the left leg member and the right leg member of the orthosis or prosthesis.

The weight of the joint and the cost of making it can be substantially reduced if use is made of links which are laminated in construction. This is illustrated in FIG. 5 where the links 14, 16 and 18 each comprise a series of laminated spaced-apart plates which can be stamped from sheet metal and vacuum-brazed together, the necessary pivot pins being assembled with the laminated links prior to the furnace treatment. Pre-plating only those surfaces of the laminated sheets which need to be joined makes it possible in such a method to produce an articulated joint without resource to any other fastening means, while the pivot pins act as assembly jigs during the brazing operation. Alternatively, the links can be laser-cut from sheet metal, but with small bridges still remaining between them and the main area of the sheet. A selective plating technique is then applied to the sheet and the link laminations on each layer so arranged that, when successive layers have been overlaid and vacuum-brazed, it will be possible to cut the completed links 14, 16 and 18 from the sheets by means of a numerically-controlled drilling programme which will cut through the bridges. In practice, each sheet will carry a number of links, and so that will provide an inexpensive method of manufacture.

If desired, additional locking means (not shown) can be provided to lock the joint in the fully-extended position of FIG. 1, the additional locking means being preferably in the form of a locking lever having a notch, groove or recess which is adapted to latch onto, in a releasable manner, a pivot member providing a pivotal connection between two of the five fixed-length links 10, 12, 14, 16, 18.

I claim:

1. An orthopaedic or prosthetic joint comprising:
   (a) a first fixed-length link member provided with two spaced-apart pivotal connections at one end thereof and a third pivotal connection remote from that end;
   (b) a second fixed-length link member pivotally connected at one end thereof to one of said first two pivotal connections on said first link member;
   (c) a third fixed-length link member pivotally connected at one end thereof to the other one of said first two pivotal connections on said first link member, said third link member being provided with a further pivotal connection at an intermediate portion thereof;
   (d) a fourth fixed-length link member arranged end-to-end with respect to said first link member but spaced therefrom by said second link member, said fourth link member being provided with two spaced-apart pivotal connections at that end nearer the first link member with one of said pivotal connections on the fourth link member being pivotally connected to said second link member at that end of the second link member remote from the first link member;
   (e) a fifth fixed-length link member pivotally connected at one end thereof to the other one of said two pivotal connections on said fourth link member and pivotally connected at the other end thereof to that end of said third link member remote from the first link member whereby the second link member on the one hand and the third and fifth link members on the other hand extend between, and connect together, the opposing ends of the first and fourth link members;
   (f) a pivotal connection on the third link member between the ends thereof;
   (g) a spring link extending between said third pivotal connection on the first link member and said further pivotal connection on the intermediate portion of the third link member, said spring link being arranged to hold the joint in any selected one of a plurality of angular positions of the fourth link member with respect to the first link member; and
   (h) joint-release means connected to said third link member whereby the joint-holding function of the spring link may be overcome by operation of the joint-release means in order to permit the fourth link member to move to another angular position with respect to the first link member.

2. An orthopaedic or prosthetic joint according to claim 1, wherein the first link member is a thigh member and the fourth link member is a shin member, and wherein the spring link is pivotally connected to a projection on the thigh member.

3. An orthopaedic or prosthetic joint according to claim 1, wherein the spring link is pivotally connected to a nose portion on the intermediate portion of the third link member.

4. An orthopaedic or prosthetic joint according to claim 1, wherein the spring link is in the form of a gas spring.

5. An orthopaedic or prosthetic joint according to claim 1, wherein the joint-release means comprise a pull member.

6. An orthopaedic or prosthetic joint according to claim 1, wherein at least one of the fixed-length link members is of laminated construction so as to reduce the weight of the joint and the cost of making it.

* * * * *